(12) United States Patent
Lee et al.

(10) Patent No.: US 8,306,796 B2
(45) Date of Patent: Nov. 6, 2012

(54) PYROTECHNIC SHOCK SIMULATION SYSTEM AND METHOD

(75) Inventors: Chi C. Lee, Riverside, CA (US);
Michael Alan Hiersche, Irvine, CA (US); Chhour M. Thong, Buena Park, CA (US)

(73) Assignee: The Boeing Company, Chicago, IL (US)

( * ) Notice: Subject to any disclaimer, the term of this patent is extended or adjusted under 35 U.S.C. 154(b) by 871 days.

(21) Appl. No.: 11/839,229

(22) Filed: Aug. 15, 2007

(65) Prior Publication Data

US 2009/0048814 A1 Feb. 19, 2009

(51) Int. Cl.
*G06G 7/48* (2006.01)

(52) U.S. Cl. .......................................... 703/6

(58) Field of Classification Search ................ 703/6
See application file for complete search history.

(56) References Cited

U.S. PATENT DOCUMENTS

| | | | |
|---|---|---|---|
| 2,809,514 A | 10/1957 | Corcoran | |
| 2,888,526 A | 5/1959 | Stockman | |
| 3,045,476 A | 7/1962 | Bell | |
| 3,206,652 A | 9/1965 | Monroe | |
| 3,345,864 A | 10/1967 | Painter et al. | |
| 3,420,098 A | 1/1969 | Painter et al. | |
| 3,842,661 A | 10/1974 | Marshall et al. | |
| 4,901,579 A | 2/1990 | Butts | |
| 5,003,811 A * | 4/1991 | Shannon et al. | 73/12.14 |
| 5,083,463 A * | 1/1992 | Marshall et al. | 73/663 |
| 5,565,626 A * | 10/1996 | Davie | 73/579 |
| 6,127,869 A * | 10/2000 | Hirasaka | 327/261 |
| 6,876,957 B1 | 4/2005 | Stewart | |
| 7,464,597 B1 * | 12/2008 | Lee et al. | 73/663 |
| 7,614,333 B2 * | 11/2009 | Quinn et al. | 89/1.1 |

FOREIGN PATENT DOCUMENTS

EP 0373943 6/1990

OTHER PUBLICATIONS

Scott, George. "Pyroshock pitfalls and pratfalls." Test Engineering & Management, Mattingly Publishing, US, vol. 68, No. 3, Jan. 1, 2006, pp. 6-7.
International Search Report, corresponding to International Patent Application No. PCT/US2008/072411, dated Dec. 4, 2008.
Written Opinion, corresponding to International Patent Application No. PCT/US2008/072411, dated Dec. 4, 2008.

* cited by examiner

*Primary Examiner* — Mary C Jacob
*Assistant Examiner* — Aniss Chad
(74) *Attorney, Agent, or Firm* — Charles L. Moore; Moore & Van Allen PLLC

(57) ABSTRACT

A system to simulate pyrotechnic shock may include a pulse or signal generator to generate a predetermined signal waveform. A signal conditioning device may be included to condition the predetermined signal waveform to produce a predetermined shock simulation for a shock test. The system may also include a power amplifier to amplify the conditioned predetermined signal waveform to a chosen amplitude to produce a selected level of shock. A shaker system produces the selected level of shock in response to an amplified signal waveform from the power amplifier. A shock measuring device measures a shock imparted to the test specimen, and an output device presents a result of the shock test on the test specimen.

31 Claims, 2 Drawing Sheets

PYROTECHNIC SHOCK SIMULATION SYSTEM AND METHOD

BACKGROUND OF THE INVENTION

The present invention relates to testing electronic equipment, or other equipment or devices with respect to withstanding shock and other environmental conditions, and more particularly to a pyrotechnic shock simulation system and method to simulate a pyrotechnic type shock similar to those experienced during the launch of a space vehicle, satellite or similar event.

Components and devices used on space vehicles, such as electronic components, mechanical devices, or other apparatus, need to be able to withstand the rigors of a space launch that may include extreme shock or vibrations such as those caused by pyrotechnic shock events, for instance, ignition, liftoff, stage separations, payload fairing separations, spacecraft separations, solid rocket motor jettisons or similar events. These shock environments or events are difficult to duplicate or simulate. Actually using explosives or pyrotechnic materials, primer cords, etc., can be time consuming and expensive to set up and difficult to control. Outsized, high-power electrodynamic exciters and impact hammers may also be used for high-energy level shock simulations; however, such devices typically require expensive modifications to simulate a high energy-level shock event such as those associated with a space launch.

BRIEF SUMMARY OF THE INVENTION

In accordance with an embodiment of the present invention, a method to simulate pyrotechnic shock may include generating a predetermined signal waveform and conditioning the predetermined signal waveform to produce a predetermined shock simulation for a shock test. The method may also include amplifying the conditioned predetermined signal waveform to a chosen amplitude to produce a selected level of shock. A field coil and a driver coil of a shaker system may be energized to produce the selected level of shock. The method may further include measuring a shock imparted to a test specimen and presenting results of the shock test on the test specimen.

In accordance with another embodiment of the present invention, a system to simulate pyrotechnic shock to test a specimen may include a pulse or signal generator to generate a predetermined signal waveform. A signal conditioning device may be included to condition the predetermined signal waveform to produce a predetermined shock simulation for a shock test. The system may also include a power amplifier to amplify the conditioned predetermined signal waveform to a chosen amplitude to produce a selected level of shock. A shaker system may produce the selected level of shock in response to an amplified signal waveform from the power amplifier. A shock measuring device measures a shock imparted to the test specimen, and an output device presents a result of the shock test on the test specimen. For purposes of this disclosure a test specimen signifies a single part or collections of parts that may define a component, device, system, or vehicle.

In accordance with another embodiment of the present invention, a system to simulate pyrotechnic shock may include a pulse or signal generator to generate a predetermined signal waveform. The system may also include an analog filter and a digital filter. The analog filter may filter the predetermined signal waveform and select levels of output at different filter intervals. The digital filter may produce a predetermined (broad) dynamic range for the shock simulation in combination with the analog filter. The system may further include a power amplifier to amplify the conditioned predetermined signal waveform to a chosen amplitude to produce a selected level of shock. A shaker system may be provided to produce the selected level of shock in response to an amplified signal waveform from the power amplifier. The system may additionally include a shock measuring device to measure a shock imparted to the test specimen. An output device may be included to present a result of the shock test on the test specimen.

In accordance with another embodiment of the present invention, a method to test a specimen may include simulating a pyrotechnic shock and imparting the simulated pyrotechnic shock to the specimen to perform a shock test. The method may also include measuring a level of the shock imparted to the specimen and presenting results of the shock test.

Other aspects and features of the present invention, as defined by the claims, will become apparent to those ordinarily skilled in the art upon review of the following non-limited detailed description of the invention in conjunction with the accompanying figures.

DETAILED DESCRIPTION OF THE INVENTION

The following detailed description of embodiments refers to the accompanying drawings, which illustrate specific embodiments of the invention. Other embodiments having different structures and operations do not depart from the scope of the present invention.

Figure 1:
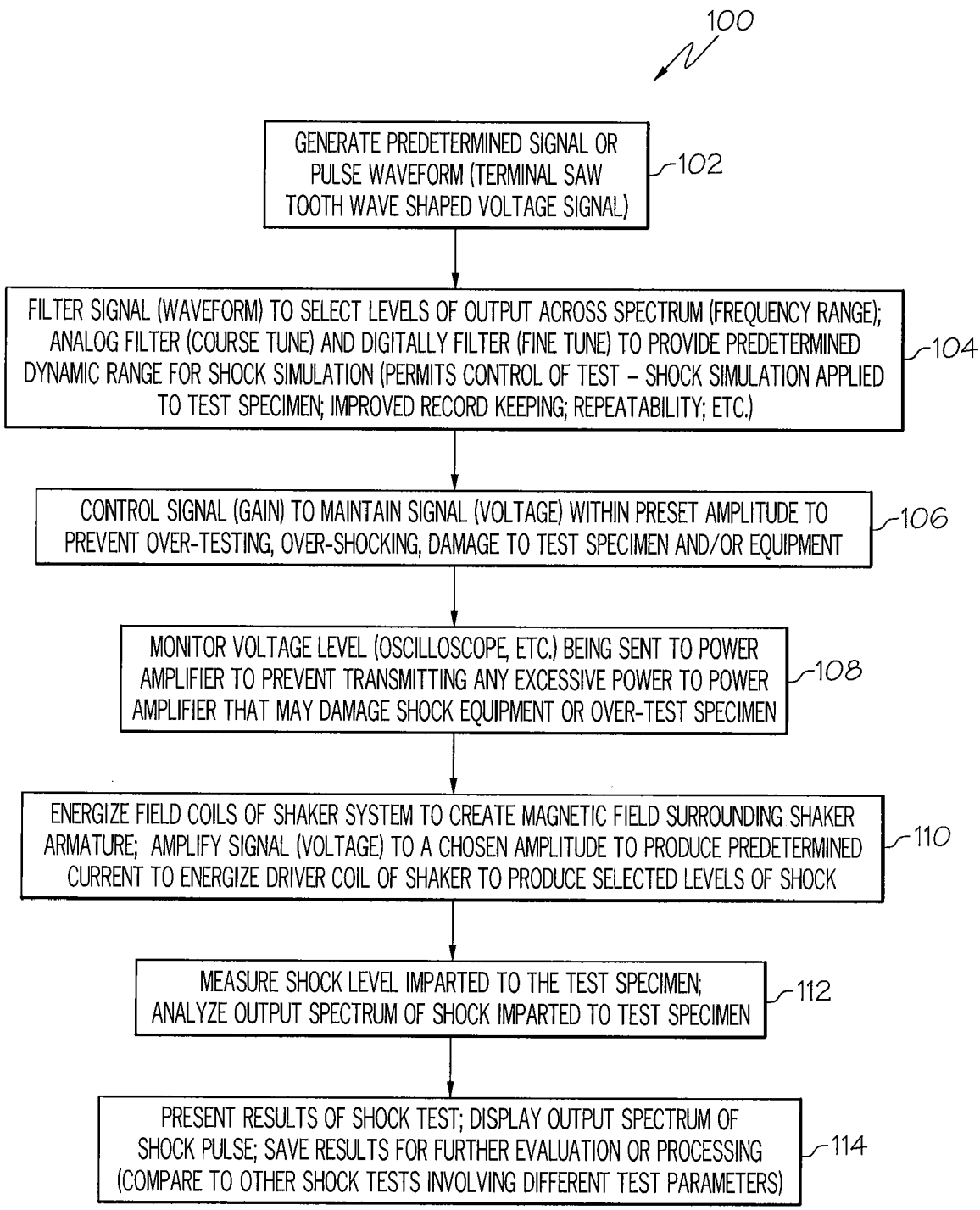
FIG. 1 is a flow chart of an example of a method to simulate pyrotechnic shock to test a specimen in accordance with an embodiment of the present invention.

FIG. 1 is a flow chart of an example of a method 100 to simulate pyrotechnic shock to test a specimen in accordance with an embodiment of the present invention. In block 102, a predetermined signal waveform or pulse waveform may be generated. The predetermined signal or pulse waveform may be a terminal saw tooth wave shaped signal or similar signal. For example, a single terminal saw tooth pulse of a few milliseconds in duration and a magnitude of several volts may be generated. A terminal saw tooth wave shape may be selected because such a waveform is superior to signals of other wave shapes in exciting all frequencies in a desired test frequency range for simulating pyrotechnic shock.

In block 104, the predetermined signal waveform may be conditioned to produce a predetermined shock simulation for a shock test. The predetermined signal waveform may be conditioned by filtering the signal waveform to select output levels across a spectrum or frequency range of the predetermined signal waveform. In accordance with an embodiment of the present invention, the predetermined signal waveform may be conditioned by filtering using an analog filter and a digital filter. The analog filter may coarse tune the signal to select output levels at different filter intervals. The digital filter may fine tune the signal waveform. The combination of digital and analog filtering provides a broader dynamic range in setting up the shock simulation. The conditioning or filtering enhances control of the test shock simulation and the level of shock imparted to the test specimen. In addition to better test control, the utilization of digital filtering may result in better record keeping and improved repeatability as described herein.

In block 106, an amplitude or gain of the conditioned or filtered signal waveform may be controlled within a preset level to prevent over-testing, over-shocking, or damage to the test specimen and/or damage to the shaker system or shock equipment.

In block 108, a voltage level of the conditioned or filtered signal waveform may be monitored to prevent a power in excess of a chosen amount from being transmitted for amplification. Monitoring the conditioned or filtered waveform permits the waveform to be limited or clipped to control the power level being amplified to prevent shocking the test specimen over a preset level (over-testing or over-shocking the test specimen), damaging the test specimen, and/or damaging the shaker system or test equipment.

In block 110, the shaker field coils are energized to create a magnetic field surrounding a shaker system armature or driver coils, a filtered voltage signal waveform may be amplified to a chosen amplitude to produce a predetermined current to energize the driver coils of the shaker system and to produce the selected level of shock force to be imparted to the test specimen.

In block 112, the level of shock imparted to the test specimen may be measured. The output spectrum of the shock imparted to the test specimen may also be analyzed using a spectrum analyzer or similar device.

In block 114, the results of the shock test may be presented. Analysis of the output spectrum of the shock pulse may be presented on a display of the spectrum analyzer. The results may be saved for further processing or analysis, such as comparison to other shock tests involving different testing parameters.

Figure 2:
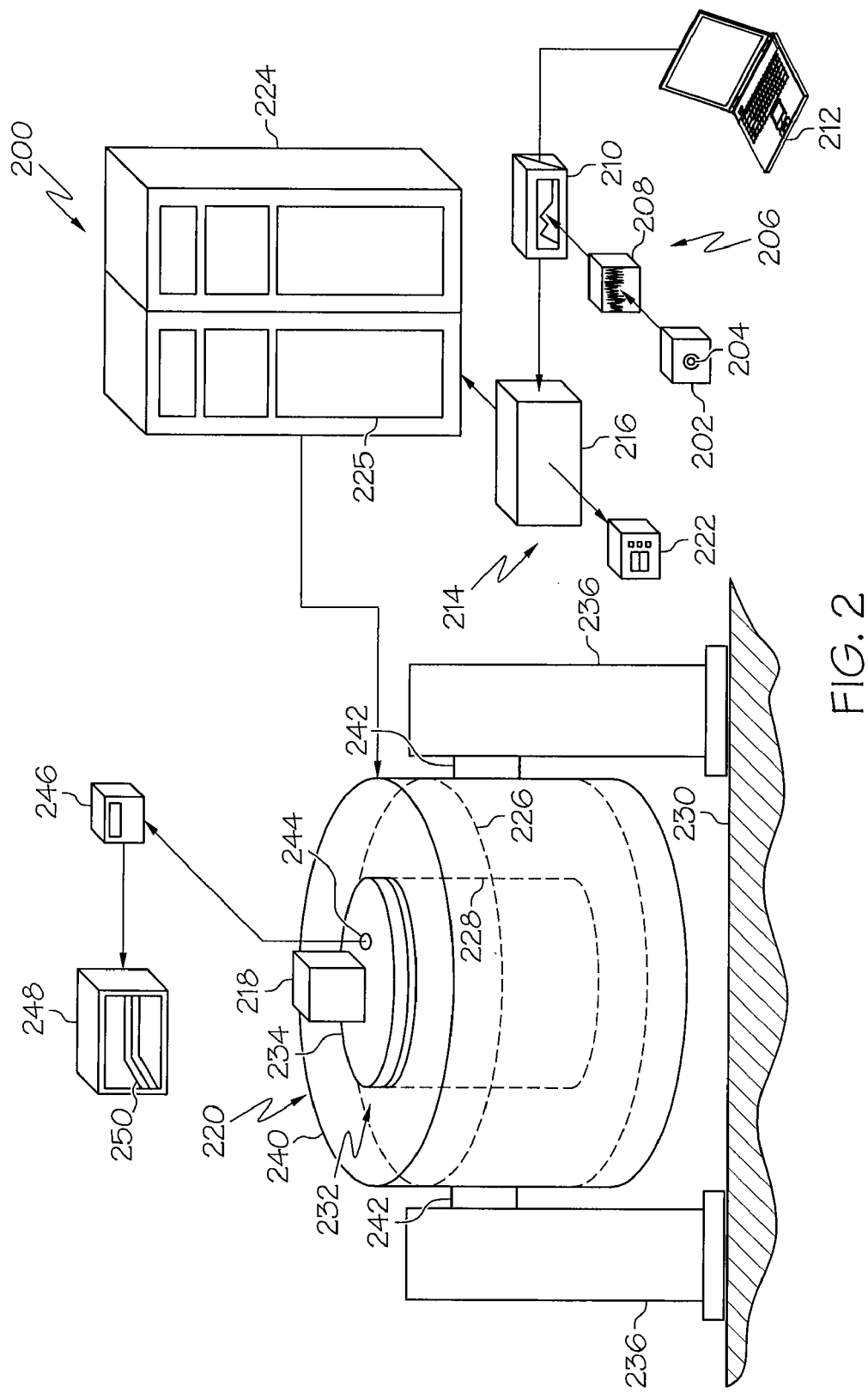
FIG. 2 is a block schematic diagram of a system to simulate pyrotechnic shock to test a specimen in accordance with another embodiment of the present invention.

FIG. 2 is a block schematic diagram of a system 200 to simulate pyrotechnic shock to test a specimen in accordance with an embodiment of the present invention. The method 100 may be performed by or embodied in the system 200. The system 200 may include a pulse or signal generator 202 to generate a predetermined pulse or signal waveform. In accordance with an embodiment of the present invention, the pulse or signal generator 202 may generate a single terminal saw tooth pulse of variable pulse duration of a few milliseconds and a magnitude of several volts. A terminal saw tooth wave shape may be selected because such a waveform is superior to signals of other wave shapes in exciting all frequencies in a desired test frequency range for simulating pyrotechnic shock. A desirable frequency range for shock tests may be between about 10 Hz and about 10,000 Hz.

The pulse or signal generator 202 may include an activation means 204, such as a push button switch or similar device, which may be operated by a user to activate the electronic circuitry in the generator 202 to generate the predetermined pulse or signal waveform.

The system 200 may include a signal conditioning device 206 or devices to condition the predetermined signal waveform or pulse waveform to produce a predetermined shock simulation for a shock test. The signal conditioning device 206 may include an analog filter 208 and a digital filter 210.

The analog filter 208 may be a ⅓ octave filter including multiple sliders set at ⅓ octave frequency intervals. The adjusting sliders are essentially variable resistors or potentiometers that allow a user to manually select the levels of output at different filter intervals. The manipulated output signal of the analog filter 208 may then be sent to an input of the digital filter 210. The analog filter 208 is advantageous for producing an ideal transient waveform from the terminal saw tooth input. The analog filter 208 may be a Bruel & Kjaer Type 5612 Spectrum Shaper as manufactured by Bruel & Kjaer Precision Instruments of Denmark or a similar analog filter.

The digital filter 210 may be a ⅓ octave digital filter. The digital filter 210 may be controlled by a computer 212, such as a notebook computer or other computing device. The computer-controllable digital filter 210 may include multistage ⅓ octave software filter sets connected in series. The digital filter 210 allows a user to select via a keyboard or mouse of the computer 212 the filter setting at different filter stages by using soft keys incorporated in the software application or by other means. The digital filter 210 may be any digital filter, such as a RANE Model RPM2 Programmable Multiprocessor, as manufactured by the Rane Corporation of Mukilteo, WA or a similar digital filter. Digital sliders may be presented on the display of the computer to permit output levels at different frequencies to be set numerically or digitally at about ¼ decibel increments and to shape the spectrum of the output signal waveform. The computer-controlled digital filter 210 provides flexibility and provides the user with improved control of the input shock levels. Additionally, the user can permanently save and maintain test records by assigning settings for each test program with a unique file name or identification. The digital controller may also function as a signal amplifier providing control of the output gain by ½ dB increments.

The combination of the digital and analog filters 208 and 210 provide a broader dynamic range in setting up the shock simulation compared to other known systems. The filters 208 and 210 also permit improved test control, better record keeping and improved repeatability.

The digital filter 210 is desirable for permitting fine tuning of the shock response spectrum. The digital filter 210 also produces tighter tolerance shock simulation results, permits minor adjustments to be made, and prior settings can be backtracked. The digital filter 210 also permits the user to save multiple files, to calibrate for various configurations and to return to the exact settings at a later time and/or date. An individual can save multiple configurations during calibration efforts and then return to the most advantageous profile.

The digital filter 210 may also significantly increase the dynamic range of the system. The filter 210 allows for improved maximum gain levels for each individual filter (higher shock levels can be obtained), and also allows for improved attenuation for each individual filter (reduces possibility of over-testing).

The digital filter 210 also has the capability to create new filters set to different frequencies than the traditional ⅓ octave filters. This feature provides more precise control. The digital filter 210 may also be utilized to control the signal output level to the power amplifier 224. This improves repeatability and allows one to change the gain by precise increments of ½ dB.

The system 200 may also include a control unit 214 coupled to an output of the digital filter 210. The control unit 214 prevents the conditioned or filtered waveform from exceeding a preset amplitude or gain. The control unit 214 may include a mixer/clipper and master gain control device 216 or a similar device to perform a signal clipping function, gain control, or signal limiting function. The mixer/clipper and master gain control device 216 may also amplify the voltage from both the analog filter 208 and the digital filters 210 and may serve as a safety check valve to prevent over-shocking, over-testing, or damaging a test specimen 218 and/or the shaker or shock equipment 220. The clipping function provides additional control of high frequency content and provides a more ideal waveform.

The master gain function of the mixer/clipper and master gain control device 216 may provide additional signal amplification. The safety check valve feature prevents unexpected signals from being transmitted to a shaker amplifier or power amplifier 224 and allows an operator to turn the system 200 off, while making adjustments and between shocks.

The clipping function of the mixer/clipper and master gain control device 216 permits clipping of high frequency content of the signal. The shaker system 220 does not respond significantly to frequency input beyond about 3 kHz. The clipping function also provides a more ideal waveform. The conditioned waveform is much smoother and slowly ramps up, compared with an abrupt transient signal not being filtered through the clipping function. This prevents the shaker amplifier or power amplifier 224 from tripping, which allows higher inputs. A limiting system associated with the power amplifier 224 does not like abrupt transient signals and may trip out. The limiting system prefers smooth signals that slowly ramp up.

The system 200 may also include a monitoring device 222 for a user to monitor a voltage level being sent to a power amplifier 224 from the mixer/clipper and master gain control device 216. The monitoring device 222 may be an oscilloscope or other device to read an output voltage from the mixer/clipper and master gain control device 216 to provide the user a visual aid for monitoring the voltage. The oscilloscope may be a digital scope including an on-screen numeric display of the output voltage from the mixer/clipper and master gain control device 216. By evaluating the voltage levels being sent to the power amplifier 224, the user can prevent any excessive power from being transmitted to the power amplifier 224 that may result in damage to the shaker or shock equipment 220 or over-testing or damage to the test specimen 218.

The monitoring device 222 or oscilloscope provides a visual aid to verify the expected shape and magnitude of the signal and permits viewing the signal before sending the waveform to the shaker amplifier or power amplifier 224.

The monitoring device 222 or oscilloscope also permits measurement of peak values of the output signal from the mixer/clipper and master gain control device 216 to verify signal output, prevent transmitting excessive power to the shaker amplifier 224, prevent over-testing the test specimen 218, and prevent exceeding limitations of shaker amplifier 224. This will reduce wear and damage of the equipment and reduce the cost of maintenance and repair.

The power amplifier 224 may be any power amplifier including generators capable of producing an alternating output current having sufficient amplitude to produce the selected level of shock imparted to the test specimen 218. The power amplifier 224 generates alternate electrical current, typically in the range of about 0 to about 500 amperes. An example of a power amplifier that may be used for power amplifier 224 may be an Unholtz-Dickie Model 2XSA series power amplifier, as manufactured by Unholtz-Dickie Corporation of Wallingford, Conn., or a similar power amplifier. The power amplifier 224 can also desirably reproduce and amplify an input signal without distortion. Additionally, the power amplifier 224 may include a direct electric current generator 225 and can supply a selected direct current to a field circuit 226 of the shaker system 220. The direct current generator 225 may be any field current supply, such as an MB Electronics model number N603, manufactured by ACG Dynamics of West Haven, Conn., or similar direct current generator capable of generating a direct electric current of approximately 300 amperes. The direct current from the power amplifier 224 may energize the shaker field coils or circuit 226 to create a magnetic field surrounding an armature or driver coil 228 of the shaker system 220.

The shaker system 220 is electrically connected to the power amplifier 224 as discussed above. The shaker system 220 may be an Unholtz-Dickie Model T1000 shaker or MB Electronic Model C-150 shaker available from Ling Electronics or ACG Dynamics, Inc., West Haven, Conn.

The shaker system 220 is rigidly supported by a large reaction mass, for example, a concrete unyielding floor 230 or similar reaction mass. The shaker system 220 provides a test platform 232 on which a test fixture 234 may be mounted. The test specimen 218 may be mounted on the test fixture 234 for shock testing.

The shaker system 200 may also include a pair of stanchions 236 mounted to the floor 230. A shaker table or equipment 240 of the shaker system 200 may be pivotably mounted to the stanchions by a trunnion 242. The shaker table 240 may be pivoted using the trunnion 242 to perform shock tests on the test specimen 218 in different axes, planes or positions.

The system 200 may additionally include a shock measuring device 244 or sensor to measure a shock force imparted to the test specimen 218. The shock measuring device 224 may also include means or circuitry for recording or storing the shock level imparted to the test specimen 218. The measuring device 244 may be an accelerometer mounted on the test fixture or any sort of device capable of measuring the shock force.

The system 200 may further include a signal conditioner 246 or signal conditioning unit. The signal conditioner 246 may supply power to the shock measuring device 244 or accelerometer and may amplify a low level signal that may be generated by the shock measuring device 244 in response to the device 244 measuring a shock force imparted to the test specimen 218.

An output device 248 may present the results of the shock test on the test specimen 218. The output device 248 may be or may include a spectrum analyzer to provide an analysis of the shock pulse imparted to the test specimen 218. The spectrum analyzer may be coupled to the signal conditioner 246. The spectrum analyzer may provide a ⅙ or 1½-octave band analysis or other analysis of the shock pulse imparted on the test specimen 218. The spectrum analyzer may include or may be connected to a display 250 for presentation of the test results or analysis for a user to monitor and to perform further analysis.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," and "includes" and/or "including" when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. A method to simulate pyrotechnic shock, comprising:
generating a predetermined signal waveform;
conditioning the predetermined signal waveform to produce a predetermined shock simulation for a shock test, wherein the conditioning the predetermined signal waveform comprises filtering the signal waveform to select levels of output of the signal waveform across a frequency range of the signal waveform, wherein filtering the signal waveform comprises:
filtering the signal waveform with an analog filter to select levels of output at different filter intervals;
filtering a filtered signal waveform from the analog filter with a digital filter to control the selected level of shock imparted to the test specimen;
amplifying the conditioned predetermined signal waveform to a chosen amplitude to produce a selected level of shock;
energizing a field coil and driver coil of a shaker system to produce the selected level of shock; and
measuring a shock imparted to a test specimen by the shaker system; and presenting results of the shock test on the test specimen.

2. The method of claim 1, wherein filtering the signal waveform comprises coarse tuning the signal waveform and fine tuning the signal waveform to produce a predetermined dynamic range for the shock simulation.

3. The method of claim 1, wherein generating the predetermined signal waveform comprises generating a saw tooth wave shaped voltage signal.

4. The method of claim 1, further comprising controlling an amplitude of the conditioned predetermined signal waveform to prevent shocking the test specimen over a predetermined level.

5. The method of claim 1, further comprising monitoring a voltage level of the conditioned predetermined signal waveform to prevent a power in excess of a chosen amount from being transmitted for amplification to prevent shocking the test specimen over a predetermined level.

6. The method of claim 1, further comprising presenting an output spectrum of the shock imparted to the test specimen.

7. The method of claim 1, further comprising:
analyzing a output spectrum of the shock imparted to the test specimen; and
presenting results of the analysis of the output spectrum of the shock to determine an ability of the test specimen to withstand forces associated with a pyrotechnic event simulated by the shock imparted to the test specimen.

8. The method of claim 1, further comprising providing the analog filter directly connected to the digital filter.

9. The method of claim 1, wherein the digital filter comprises a $1/3$ octave digital filter.

10. The method of claim 1, wherein the digital filter comprises multi-stage software filter sets connected in series, wherein the digital filter is allowed to be set at different filter stages using a computer.

11. A system to simulate pyrotechnic shock to test a specimen, comprising:
a pulse or signal generator to generate a predetermined signal waveform;
a signal conditioning device to condition the predetermined signal waveform to produce a predetermined shock simulation for a shock test, wherein the signal conditioning device comprises:
an analog filter to filter the predetermined waveform from the pulse or signal generator to select levels of output at different filter intervals;
a digital filter to receive an output signal from the analog filter to control the selected level of shock;
a power amplifier to amplify the conditioned predetermined signal waveform from the digital filter to a chosen amplitude to produce a selected level of shock;
a shaker system to produce the selected level of shock in response to an amplified signal waveform from the power amplifier;
a shock measuring device to measure a shock imparted to the test specimen; and
an output device to present a result of the shock test on the test specimen.

12. The system of claim 11 further comprising:
a coarse tuning device to tune the predetermined signal waveform; and
a fine tuning device to receive an output from the coarse tuning device to produce a predetermined dynamic range for the shock simulation.

13. The system of claim 11, wherein the pulse or signal generator comprises a voltage generator to produce a saw tooth wave shaped voltage signal.

14. The system of claim 11, further comprising a control unit to prevent the predetermined waveform from exceeding a preset amplitude.

15. The system of claim 14, wherein the control unit to prevent the predetermined waveform from exceeding the preset amplitude comprises a mixer/clipper and master gain control device.

16. The system of claim 11, further comprising a monitoring device to monitor a voltage level of the conditioned predetermined signal waveform being sent to the power amplifier.

17. The system of claim 11, wherein the shock measuring device comprises an accelerometer.

18. The system of claim 11, further comprising a signal conditioner to supply power to the shock measuring device and to amplify a signal from the shock measuring device.

19. The system of claim 11, further comprising a spectrum analyzer to analyze the shock imparted to the test specimen.

20. A method to test a specimen, comprising using the system of claim 11 to test the specimen.

21. A system to simulate a pyrotechnic shock to test a specimen, comprising:
a pulse or signal generator to generate a predetermined signal waveform;
an analog filter to filter the predetermined signal waveform and to select levels of output at different filter intervals across a frequency range of the signal waveform;
a digital filter to receive an output from the analog filter to produce a predetermined dynamic range for the shock simulation in combination with the analog filter;
a master gain control device to receive an output from the digital filter;
a power amplifier to amplify a filtered predetermined signal waveform from the master gain control device to a chosen amplitude to produce a selected level of shock;
a shaker system to produce the selected level of shock in response to an amplified signal waveform from the power amplifier;
a shock measuring device to measure a shock imparted to the test specimen; and
an output device to present a result of the shock test on the test specimen.

22. The system of claim 21, further comprising a mixer/clipper and master gain control device to prevent the predetermined waveform from exceeding a preset amplitude.

23. The system of claim 21, further comprising an oscilloscope to monitor a voltage level of the filtered predetermined signal waveform being sent to the power amplifier.

24. The system of claim 21, further comprising a spectrum analyzer to analyze the shock imparted to the test specimen.

25. A method to test a specimen, comprising:
generating a predetermined signal waveform;
conditioning the predetermined signal waveform to produce a predetermined shock simulation for a shock test, wherein the conditioning the predetermined signal waveform comprises filtering the signal waveform to select levels of output of the signal waveform across a frequency range of the signal waveform, wherein filtering the signal waveform comprises:
filtering the signal waveform with an analog filter to select levels of output at different filter intervals;
filtering a filtered signal waveform from the analog filter with a digital filter to control the selected level of shock imparted to the test specimen;
amplifying the conditioned predetermined signal waveform to a chosen amplitude to produce a selected level of shock;
energizing a field coil and driver coil of a shaker system to produce the selected level of shock; and
measuring a shock imparted to a test specimen by the shaker system; and presenting results of the shock test on the test specimen.

26. The method of claim 25, further comprising simulating a pyrotechnic shock for testing the test specimen.

27. The method of claim 25, wherein generating the predetermined signal waveform comprises generating a saw tooth wave shaped voltage signal.

28. A method to test a specimen, comprising:
simulating a pyrotechnic shock comprising conditioning a predetermined signal waveform to produce a predetermined shock simulation for a shock test by filtering the signal waveform to select levels of output of the signal waveform across a frequency range of the signal waveform, wherein conditioning the predetermined signal waveform comprises:
filtering the signal waveform with an analog filter to select levels of output at different filter intervals;
filtering a filtered signal waveform from the analog filter with a digital filter to control the selected level of shock imparted to the test specimen;
imparting the simulated pyrotechnic shock to the specimen to perform a shock test;
measuring a level of the shock imparted to the specimen; and
presenting results of the shock test.

29. The method of claim 28, wherein simulating the pyrotechnic shock comprises:
generating a predetermined signal waveform;
amplifying the conditioned predetermined signal waveform to a chosen amplitude to produce a selected level of shock; and
energizing a field coil and driver coil of a shaker system to produce the selected level of shock.

30. The method of claim 29, further comprising coarse tuning the signal waveform and fine tuning the signal waveform to produce a predetermined dynamic range for the shock simulation.

31. The method of claim 29, further comprising controlling an amplitude of the conditioned predetermined signal waveform to prevent shocking the test specimen over a predetermined level.

* * * * *